United States Patent
Hasegawa

(10) Patent No.: US 9,597,268 B2
(45) Date of Patent: *Mar. 21, 2017

(54) SURFACE-TREATED AND PLATE-LIKE POWDER FOR COSMETIC COMPOSITIONS AND SOLID POWDERY COSMETIC COMPOSITION BLENDED THEREWITH

(71) Applicant: MIYOSHI KASEI, INC., Saitama-shi, Saitama (JP)

(72) Inventor: Yukio Hasegawa, Saitama (JP)

(73) Assignee: MIYOSHI KASEI, INC., Saitama (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/424,226

(22) PCT Filed: Dec. 26, 2012

(86) PCT No.: PCT/JP2012/008346
§ 371 (c)(1),
(2) Date: Feb. 26, 2015

(87) PCT Pub. No.: WO2014/102863
PCT Pub. Date: Jul. 3, 2014

(65) Prior Publication Data
US 2015/0257988 A1   Sep. 17, 2015

(51) Int. Cl.
| | | |
|---|---|---|
| *A61K 8/89* | (2006.01) | |
| *A61K 8/25* | (2006.01) | |
| *A61Q 1/02* | (2006.01) | |
| *A61Q 5/02* | (2006.01) | |
| *A61K 8/02* | (2006.01) | |
| *A61K 8/26* | (2006.01) | |
| *C09C 3/12* | (2006.01) | |
| *A61K 8/29* | (2006.01) | |
| *A61K 8/892* | (2006.01) | |
| *A61K 8/891* | (2006.01) | |
| *A61Q 1/10* | (2006.01) | |
| *A61Q 1/12* | (2006.01) | |

(52) U.S. Cl.
CPC .......... *A61K 8/0258* (2013.01); *A61K 8/022* (2013.01); *A61K 8/0241* (2013.01); *A61K 8/0254* (2013.01); *A61K 8/25* (2013.01); *A61K 8/26* (2013.01); *A61K 8/29* (2013.01); *A61K 8/891* (2013.01); *A61K 8/892* (2013.01); *A61Q 1/02* (2013.01); *C09C 3/12* (2013.01); *A61K 2800/614* (2013.01); *A61K 2800/624* (2013.01); *A61Q 1/10* (2013.01); *A61Q 1/12* (2013.01)

(58) Field of Classification Search
None
See application file for complete search history.

(56) References Cited

U.S. PATENT DOCUMENTS 5,744,126 A     4/1998   Horino et al.
2012/0171136 A1* 7/2012 Sonoyama .............. A61Q 1/02
                                                424/63

FOREIGN PATENT DOCUMENTS

| EP | 1 579 841 A1 | 9/2005 | |
|---|---|---|---|
| EP | 2 266 532 A2 | 12/2010 | |
| EP | 2266532 A2 * | 12/2010 | ............ A61K 8/895 |
| JP | S45-002915 B1 | 1/1970 | |
| JP | 45-18999 B1 | 6/1970 | |
| JP | S63-152308 A | 6/1988 | |
| JP | H08-6035 B2 | 1/1996 | |
| JP | 2582275 B2 | 2/1997 | |
| JP | H09-48716 A | 2/1997 | |
| JP | H09-255528 A | 9/1997 | |
| JP | H10-251123 A | 9/1998 | |
| JP | 3079395 B2 | 8/2000 | |
| JP | 2002-128637 A | 5/2002 | |
| JP | 2004-315468 A | 11/2004 | |
| JP | 3707758 B2 | 10/2005 | |
| JP | 2006-057054 A | 3/2006 | |
| JP | 2006-206496 A | 8/2006 | |
| JP | 3963635 B2 | 8/2007 | |
| JP | 2009-209139 A | 9/2009 | |
| JP | 2010-163375 A | 7/2010 | |

(Continued)

OTHER PUBLICATIONS

Sep. 16, 2015 Reasons for Rejections issued in Japanese Patent Application No. 2014-553883.

(Continued)

*Primary Examiner* — H. Sarah Park
(74) *Attorney, Agent, or Firm* — Oliff PLC

(57) ABSTRACT

A plate-like powder for cosmetics, powder is surface treated with a silicone gel, enhancing moldability and impact resistance of a solid powdery cosmetic composition as well as a solid powdery cosmetic composition. The surface-treated powder exhibits smooth and light touchiness, has moist usability, and excellent adhesion to skin. The surface-treated powder is blended into a powdery cosmetic composition, enhancing moldability and impact resistance of the composition and removed by an applicator. The powder is an inorganic powder, an organic powder or a composite powder, and silicone gel is obtained by hydrolyzing and condensing an organopolysiloxane containing at least a diorgano polysiloxane having reactive opposite ends by the following formula (1) and either a silane coupling agent of the following formula (2) having at least two hydrolyzable groups per one molecule or a reactive organo polysiloxane having the following formula (3) as a crosslinking agent

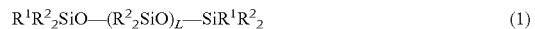 (1)

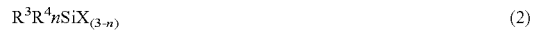

(2)

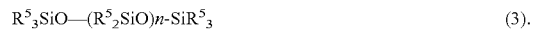

(3).

29 Claims, No Drawings

(56) References Cited

FOREIGN PATENT DOCUMENTS

| JP | 2011-001332 A | 1/2011 |
|---|---|---|
| JP | 2011-011988 A | 1/2011 |
| JP | 2012-197265 A | 10/2012 |
| WO | 2014/102863 A1 | 7/2014 |

OTHER PUBLICATIONS

Amendments to Sep. 16, 2015 Reasons for Rejection issued in Japanese Patent Application No. 2014-553883.
Argument to Sep. 16, 2015 Reasons for Rejection issued in Japanese Patent Application No. 2014-553883.
Feb. 5, 2013 International Search Report issued in International Application No. PCT/JP2012/008345.
Feb. 5, 2013 Written Opinion issued in International Application No. PCT/JP2012/008345.
Nov. 13, 2015 Amendments to Reasons for Rejections issued in Japanese Patent Application No. 2014-553882.
Nov. 13, 2015 Reasons for Rejections issued in Japanese Patent Application No. 2014-553882.
Mar. 29, 2016 Search Report issued in European Patent Application No. 12891123.7.
Nov. 13, 2015 Arguments to Reasons for Rejection in Japanese Patent Application No. JP-2014-553882.
Feb. 5, 2013 International Search Report issued in International Patent Application No. PCT/JP2012/008346.
Feb. 5, 2013 Written Opinion issued in International Patent Application No. PCT/JP2012/008346.
Jan. 18, 2016 Reasons for Rejection issued in Japanese Patent Application No. 2014-553883.
May 19, 2016 Office Action issued in Japanese Patent Application No. 2016-022292.
May 18, 2016 Invitation Pursuant to Rule 63(1) EPC issued in European Patent Application No. 12 891 116.1.
Jul. 13, 2016 Response to Invitation Pursuant to Rule 63(1) EPC (dated May 18, 2016) issued in European Patent Application No. 12 891 116.1-1458 based on PCT/2012/008346.
Aug. 9, 2016 Office Action Issued in U.S. Appl. No. 14/424,091.
May 19, 2016 Reasons for Rejection issued in Japanese Patent Application No. 2016-022291.
Jan. 18, 2016 Reasons for Rejection issued in Japanese Patent Application No. 2014-553882.
Apr. 15, 2016 Communication pursuant to Rules 70(2) and 70a(2) EPC issued in European Patent Application No. 12891123.7.
Sep. 26, 2016 Extended European Search Report issued in Application No. 12891116.1.
Barrere, M., et al. "Anionic Polymerization of Octamethylcyclotetrasiloxane in Miniemulsion II. Molar Mass Analyses and Mechanism Scheme." Polymer, Elsevier Science Publishers B.V, GB, vol. 42, No. 17, Aug. 1, 2001, pp. 7239-7246.
Nikipedia, free encyclopedia. "Shore Durometer." Aug. 2, 2016, XP055294993, URL:https://en.wikipedia.org/w/windex.php?title=Shore_durometer&printable=yes[retrieved on Aug. 11, 2016].

\* cited by examiner

SURFACE-TREATED AND PLATE-LIKE POWDER FOR COSMETIC COMPOSITIONS AND SOLID POWDERY COSMETIC COMPOSITION BLENDED THEREWITH

TECHNICAL FIELD

The present invention relates to a plate-like powder for cosmetic compositions, which is surface-treated with a silicone gel and has good usability and effects of enhancing moldability and impact resistance of a solid powdery cosmetic composition. The invention also relates to a solid powdery cosmetic composition containing such a powder. The surface-treated powder according to the present invention exhibits smoothness and light touch, and possesses moist usability peculiar to the silicone gel and excellent adhesion to skin. Further, the plate-like cosmetic powder can prevent cutting and cracking of a cosmetic composition molded in a solid state in a dish-shaped vessel by a dry type molding method or a wet type molding method. The cosmetic composition containing such a powder is well removed by an applicator, and has good stability with lapse of time.

BACKGROUND ART

The solid powdery cosmetic composition is a cosmetic material that is generally mold filled into a dish-shaped vessel, which is fitted into a compact container. Since it has good portability, such is widely used as makeup cosmetics such as a foundation, an eye shadow, etc. As to such a solid powdery cosmetic composition, a cosmetic base material in which an oily agent is added and dispersed into a powder system including a coloring pigment, a body pigment, a glittering pigment, a spherical powder, etc. is mold filled in a dish-shaped container made of a metal such as aluminum or the like or a plastic.

Further, solid powdery cosmetic compositions are frequently carried, while put in a hand bag or the like. If the molded product has poor impact resistance, the molded product may be cracked or broken when it is dropped on a floor or when it is carried, while put in the hand bag or the like. Therefore, the product must reach such a level as assuring the impact resistance under use condition in an ordinary life. In addition, since a surface of the molded product of the solid powdery cosmetic composition is rubbed off with a small tool such as sponge puff or brush, which is applied onto a skin, a rubbed state onto the small tool and usability such as a skin-applied feeling are important qualities for the product.

The usability of such a solid powdery cosmetic composition is not only influenced by kinds, particle diameters, particle shapes and chemical compositions of powders blended and an oily agent as a binder, but also the usability frequently depends upon a method of mold filling a preparation thereof. Particularly, in order to assure the impact resistance, it is important to appropriately select a combination of them.

In case of a cosmetic preparation containing a large amount of an elastic and good-touch spherical powder, a flaky powder and a glittering powder having a high aspect ratio, etc., the moldability and the impact resistance are deteriorated. So, the kinds of powders and the kind of the oily agent blended as well as the molding method have been examined.

As the method of mold filling the solid powdery cosmetic composition, a method in which a base material of the cosmetic composition composed mainly of the powders is filled in a dish-like vessel and the resultant is compression molded (so-called press molding method) is commonly used. However, in this press molding method, it may be that air remains inside the molded product depending upon the composition of the cosmetic base material, which causes problems of molding disorders such as reduction in the impact resistance, peeling or cutting. In order to avoid such problems, a wet type molding method is often used (Patent documents 1 and 2). Further, a method in which the impact resistance is enhanced by surface-treating the powder has been examined (Patent documents 3 and 4).

PRIOR ART DOCUMENTS

Patent Documents (Patent document 1) JP-A 09-255528
(Patent document 2) JP-A 2002-128637
(Patent document 3) JP-A 2009-209139
(Patent document 4) JP-A 2011-11988

DISCLOSURE OF THE INVENTION

Problems to be Solved by the Invention

Nevertheless, development of surface-treated powders for solid powdery cosmetic compositions, which powders have good impact resistance and excellent usability such as spreadability and smoothness has been desired. Therefore, an object of the present invention is to provide a plate-like powder for cosmetic compositions, which powder exhibits usability with lightness and smoothness and good impact resistance and gives a uniformly molded product with good removability by an applicator, moist usability and excellent adhesion to skin when it is incorporated into a solid powdery cosmetic composition. The invention also provides a solid powdery cosmetic composition blended therewith.

Measures for Solving the Problems (i) The present invention relates to a plate-like powder for a cosmetic composition, the powder being surface treated with a silicone gel and having an effect of enhancing moldability and impact resistance of the solid powdery cosmetic composition.

In the following, preferred embodiments of the above powder surface-treated with the silicone gel according to the present invention can be recited.

(ii) The plate-like powder for the cosmetic composition set forth in (i), wherein the powder is an inorganic powder, an organic powder or a composite powder thereof.

(iii) The plate-like powder surface-treated for the cosmetic composition as set forth in (i) or (ii), wherein the silicone gel is one obtained by hydrolyzing and condensing an organopolysiloxane containing at least a diorgano polysiloxane having reactive opposite ends represented by the following formula (1) and either a silane coupling agent of the following formula (2) having at least two hydrolyzable groups per one molecule or a reactive organo polysiloxane having the following formula (3) as a crosslinking agent.

(Chemical formula 1)

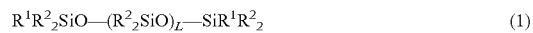

(R1 is a hydrolyzable group which is any of a hydroxyl group, an amino group, acetoxy group, an alkoxy group and a hydrogen atom, R2 is a non-substituted or substituted C1 to C20 monovalent hydrocarbon group, and L is 3 to 10,000)

(Chemical formula 2)

$$R^3R^4{}_nSiX_{(3-n)} \qquad (2)$$

(R3 is a group selected from a C1 to C20 monovalent hydrocarbon group, an amino group, an aminoethyl group, a mercapto group, an isocyanate and a phenyl group, R4 is a group selected from a C0-C3 monovalent lower alkyl group and a phenyl group, X is a hydroxyl group or an alkoxy group, and n is 0 or 1).

(Chemical formula 3)

$$R^5{}_3SiO—(R^5{}_2SiO)n-SiR^5{}_3 \qquad (3)$$

(R5 is a hydrolyzable group or a non-substituted or substituted C1-C20 monovalent hydrocarbon group, the hydrolyzable group is any of a hydroxyl group, an amino group, an acetoxy group, an alkoxyl group and a hydrogen atom, n is 3 to 1,000, and at least three hydrolyzable groups are provided in one molecule).
(iii) The cosmetic powder set forth in any one of [1] and (i) to (ii), wherein the silicone gel has a complex modulus of 3,000 to 100,000 Pa, and a loss coefficient tan δ is 1.0 to 2.5 in measurement of a dynamic viscoelasticity under a distortion factor of 17% at 25° C. and a shear frequency of 4 Hz.
(iv) The cosmetic powder set forth in any of [1] and (i) to (iii), wherein the diorganopolysiloxane of the formula (1) is a dimethiconol.
(v) The cosmetic powder set forth in (iv), wherein a water emulsion obtained by mechanically emulsifying the dimethiconol having a number of dimethyl siloxane units L of 3 to 1,000 in the formula (1) is used as a starting material for the surface treatment.
(vi) The cosmetic powder set forth in (iv), wherein a water emulsion obtained by emulsion polymerizing the dimethiconol having a number of dimethyl siloxane units L of 3 to 1,000 in the formula (1) is used as a starting material for the surface treatment.
(vii) The cosmetic powder set forth in (iv), wherein a water emulsion of the dimethiconol obtained by emulsion polymerizing octamethyl cyclotetrasiloxane as a starting material is used as a starting material for the surface treatment.
(xii) The cosmetic powder set forth in any of (ix) to (xi), wherein a surface active agent is contained in the water emulsion of the dimethiconol, and said surface active agent contains at least an acylated amino acid.
(xiii) The cosmetic powder set forth in (xii), wherein a mixing weight ratio (B)/(A)×100 between the weight (B) of the surface active agent and that (A) of the dimethiconol in the water emulsion of the dimethiconol is less than 6.0.
(xiv) The cosmetic powder set forth in any of (i) to (xiii), wherein the organic group R3 of the silane coupling agent of the formula (2) is either an amino group or a phenyl group.
(xv) The cosmetic composition set forth in any of (i) to (xiv), which is obtained by hydrolyzing and condensing at least partially the diorgano polysiloxane of the above (1) having the reactive opposite ends and the silane coupling agent of the above (2) or the organo polysiloxane of the above (3), in a state that a mixed state of a water-soluble solvent and a powder to be surface treated is in either a capillary or slurry state, in a step of separately adding or simultaneously adding the diorgano polysiloxane and the silane coupling agent or the organo polysiloxane.
The present invention further relates to a solid powdery cosmetic composition containing 0.1 wt % or more of the cosmetic plate-like powder surface-treated with the silicone gel set forth in any of (i) to (xv).

Effects of the Invention

The plate-like cosmetic powder surface-treated with the silicone gel according to the present invention is a powder that can exhibit smooth and light touch, moist usability peculiar to the silicone gel, and is excellent in adhesion to skin. The cosmetic composition into which the powder is mixed can provide a solid powdery cosmetic composition that has excellent moldability and impact resistance, and is well removable with an applicator.

EMBODIMENTS TO CARRY OUT THE INVENTION

In the following, [1] the plate-like powder for cosmetics, surface-treated with the silicone gel, [2] the method for producing the plate-like powder for cosmetics, surface-treated with the silicone gel, and [3] the solid powdery cosmetic composition containing the surface-treated powder, which is surface-treated with the above silicone gel will be explained in this order with respect to the present invention.
[1] Surface-Treated Powder Surface-Treated with a Silicone Gel, which Gives Excellent Moldability and Impact Resistance The surface-treated powder according to the present invention is a surface-treated powder which is surface-treated with a silicone gel, and the powder surface-treated with the silicone gel in which the powder is a plate-like powder or glittering powder, preferably a plate-like cosmetic powder which is surface-treated with the silicone gel, using a water emulsion of dimethiconol as a starting material. When the surface-treated powder is incorporated into the solid powdery cosmetic composition, the moldability and the impact resistance of the solid powdery cosmetic composition are enhanced with good usability.
[Powder to be Surface-Treated]

The plate-like powder for cosmetics may be any of an inorganic powder, an organic powder or an inorganic/inorganic composite powder, an inorganic/organic composite powder or an organic/organic composite powder as usually used, and only one kind may be used or two or more kinds thereof may be used in an appropriately combined manner. As to the kind of the powder, the geometric shape of the powder particles is a plate-like shape or a flaky shape, for example. The plate-like powder referred to in the present invention means a powder having a particle shape in which an aspect ratio (diameter/thickness in particles) is 2 or more.

The average particle diameter is preferably 1 to 700 μm, more preferably 5 to 600 μm. If the particle diameter is less than 1 μm, the powder is strongly agglomerated with the silicone gel, so that usability and light touch feeling may be deteriorated. If it is more than 700 μm, an effect of enhancing the impact resistance may not be obtained. Note that the average particle diameter is measured by appropriately selecting a principle of a microscopic method, a light scattering method, a laser diffraction method, a liquid phase precipitation method, an electric resistance method or the like, depending upon the shapes of the powder particles.

In the present invention, the plate-like powder is used as a powder to be surface-treated with the silicone gel. Any plate-like powder usable in the common cosmetic compositions may be as a preferred plate-like powder to be used in the present invention. Specifically, recitation is made of white inorganic pigments such as titanium oxide, zinc oxide, barium sulfate, etc.; white extender pigments such as silica, talc, muscovite, phlogopite, lepidolite, biotite, synthetic mica, sericite, synthetic sericite, kaolin, silicon carbide, bentonite, smectite, aluminum oxide, magnesium oxide, calcium carbonate, magnesium carbonate, hydroxy apatite, bismuth oxychloride, etc.; boron nitride, mica coated with titanium oxide, bismuth oxychloride coated with titanium oxide, synthetic phlogopite coated with titanium oxide, glass powder, glass powder coated with titanium oxide, iron oxide mica titanium, black iron oxide mica titanium, iron oxide-black iron oxide-coated mica titanium, indigo blue-coated mica titanium, carmine-coated mica titanium, carmine-indigo blue coated mica titanium, iron oxide-carmine coated mica titanium, iron oxide-indigo blue-coated mica titanium, chromium oxide-coated mica titanium, black iron oxide-coated mica titanium, bismuth oxychloride, argentine, iron oxide-coated mica, organic pigment-coated mica titanium, multilayer coated mica titanium, and silicic acid-titanium oxide coated mica. As a glittering powder, recitation is made of glittering powders such as colcothar-coated silicic anhydride, titanium oxide-coated silicic anhydride, titanium oxide-coated aluminum oxide, boron nitride, aluminum powder, polyethylene terephthalate-aluminum-epoxy laminated powder, etc.; glittering powders of lame such as polyethylene terephthalate-aluminum-epoxy laminated powder, polyethylene terephthalate-polyolefin laminated film powder, polyethylene terephthalate-polymethyl methacrylate laminated film powder; PMMA powder, PTFE powder, a metal soap, cellulose, an alkyl phosphate, organic low-molecular powders such as N-acyl lysin, etc. One kind or more of them can be used.

The average particle diameters of the plate-like powder and the plate-like glittering powder are preferably 1 to 700 μm, and more preferably 5 to 600 μm. If the particle diameters are less than 1 μm, it may be that aggregation is strongly caused with the silicone gel, and usability and light touch are deteriorated. If the particle diameters are more than 700 μm, an effect of increasing the impact resistance may not be exhibited.

Further, in order to improve affinity and adherence with the surface-treating agent, the powder to be surface-treated in the present invention may be coated with at least one kind of oxides or hydrous oxides of aluminum, calcium, magnesium, cerium, silicon, zirconium, titanium, zinc, iron, cobalt, manganese, nickel and tin, for example.

As commercially available plate-like powders for cosmetics, recitation is made of, for example, fit powder FK300S (manufactured by Yamaguchi Unmo Industries, Ltd.), talc CT-35, talc EX-10 (manufactured by Yamaguchi Mica Co., Ltd.), Himalaya talc H-400 (manufactured by Asada Seifun Co., Ltd.), synthetic mica PDM-FE, synthetic mica PDM-10S, synthetic mica PDM-20L, etc. (manufactured by Topy Industries Ltd.), Eight pearl 300S, Eight pearl FK-1000 (Kakuhachi Gyorinhaku Co., Ltd.), etc. 33As the plate-like glittering powders, recitation is made of titanium oxide-coated micas including Flamenco Sparkle series, Timica series (hereinbefore, manufactured by BASF Co., Ltd.), Timiron Super series (Merck Co., Ltd.), Cloisonne series being iron oxide-iron blue coated mica titanium, and Duo chrome series (hereinbefore, manufactured by BASF Co., Ltd.). As the titanium oxide-coated synthetic phlogopite, recitation is made of Prominence series (manufactured by Topy Industries Ltd.). As titanium oxide-coated glass powder, Metashine series (manufactured by Nippon Sheet Glass Co., Ltd.) is recited. As the polyethylene terephthalate-aluminum-epoxy laminated powder, DC glitter series and AS glitter series (hereinbefore, manufactured by Fujiyama Sangyou Co., Ltd.) are recited. As the multilayer-coated mica titanium, Timiron Splendid series (manufactured by Merck Co., Ltd.) is recited. As the titanium oxide-coated silicic anhydride, XIRONA INDIAN SUMMER (manufactured by Merck Co., Ltd) is recited. As the titanium oxide-coated talc, SILSEEM SILKY series (Nihon Koken Kogyou Co., Ltd.) is recited. As other plate-like powders, plate-like powders such as EXCEL MICA (aluminum hydroxide-coated mica), PLV (zinc oxide and hydroxy apatite coated mica), SXI-5 (silica bead-coated mica), SXI-9 (alumina bead-coated mica), etc. (hereinbefore, manufactured by Miyoshi Kasei Co., Ltd.) are recited.

[Method of Producing Silicone Gel]

The silicone gel referred to in the present invention is one obtained from a curable liquid silicone composition, and the curing involves a curing by an addition reaction and a curing by a condensation reaction. As for the addition reaction, recitation is made of for example, a silicone gel obtained by an addition reaction between an organo polysiloxane having at least two monovalent olefinic unsaturated groups in one molecule and an organo hydrogen polysiloxane having at least three hydrogen atoms bonded to silicon atoms in one molecule under a platinum-based catalyst. As for the condensation reaction, recitation is made of a silicone gel obtained by condensation polymerizing a liquid silicone composition composed of an organo polysiloxane having at least two hydroxyl groups bonded to silicon groups in one molecule and an organo hydrogen polysiloxane having at least three hydrogen atoms bonded to silicon atoms in one molecule, in the presence of a condensation catalyst. The silicone gel obtained by either of the above methods will do, and a preferred method for obtaining the silicone gel in the present invention is one using the condensation reaction. A preferred embodiment is a polymer with a finely 3-dimensional crosslinked structure of a diorgano polysiloxane obtained by a method of hyrolyzing and condensing an organopolysiloxane containing at least a diorgano polysiloxane having reactive opposite ends represented by the following formula (1) and either a silane coupling agent of the following formula (2) having at least two hydrolyzable groups per one molecule or a reactive organo polysiloxane having the following formula (3) as a crosslinking agent.

(Chemical formula 1)

$$R^1R^2_2SiO\text{---}(R^2_2SiO)_L\text{---}SiR^1R^2_2 \qquad (1)$$

(R1 is a hydrolyzable group which is any of a hydroxyl group, an amino group, acetoxy group, an alkoxy group and a hydrogen atom, R2 is a non-substituted or substituted C1 to C20 monovalent hydrocarbon group, and L is 3 to 10,000)

(Chemical formula 2)

$$R^3R^4nSiX_{(3-n)} \qquad (2)$$

(R3 is a group selected from a C1 to C20 monovalent hydrocarbon group, an amino group, an aminoethyl group, a mercapto group, an isocyanate and a phenyl group, R4 is a group selected from a C0-C3 monovalent lower alkyl group and a phenyl group, X is a hydroxyl group or an alkoxy group, and n is 0 or 1).

(Chemical formula 3)

$$R^5_3SiO\text{---}(R^5_2SiO)n\text{-}SiR^5_3 \qquad (3)$$

(R5 is a hydrolyzable group or a non-substituted or substituted C1-C20 monovalent hydrocarbon group, the hydrolyzable group is any of a hydroxyl group, an amino group, an acetoxy group, an alkoxyl group and a hydrogen atom, n is 3 to 1,000, and at least three hydrolyzable groups are provided in one molecule).

Here, as R2 in the formula, recitation is made of for example, alkyl groups such as a methyl group, an ethyl group, a proply group, a butyl group, a pentyl group, a hexyl group, a heptyl group, an octyl group, a nonyl group, a decyl group, an undecyl group, a dodecyl group, a tetradecyl group, a pentadecyl group, a hexadecyl group, a heptadecyl group, an octadecyl group, a nonadecyl group, an eicosyl group, a henicosyl group, a dodecyl group, a tricosyl group, a tetrasyl group, a triacotyl group, etc.; cycloalkyl groups such as a cyclobutyl group, a cyclopentyl group, a cyclohexyl group, a cycloheptyl group, etc.; aryl groups such as a phenyl group, a tolyl group, a naphthyl group, etc.; aralkyl groups such as a benzyl group, a phenethyl group, a β-phenylpropyl group, etc.; and hydrocarbons in which a part or an entire part of hydrogen atoms bonded to carbon atoms of these groups are replaced by atoms such as halogen atoms (fluorine atoms, chlorine atoms, bromine atoms or iodine atoms) and/or substituent groups such as an acryloyloxy group, a methacryloyloxy group, an epoxy group, a glycidoxy group, an amino group, a mercapto group, a carboxyl group, etc.

Different from silicone elastomers, the silicone gel to treat the surfaces of the cosmetic powder may take the form of particles instead of an elastic solid. In this case, the surface treatment may be effected for any shape of the silicone gel. The surface treatment referred to in the present invention means a state in which surfaces of the powdery particles are attached or coated with the silicone gel. The density or the shape of the silicone gel attached onto the surfaces of the powdery particles is not particularly limited, so long as the effects to be accomplished by the present invention are exhibited. That is, it may be that the particulate silicone gel is sparsely attached to the surfaces of the powdery particles, or the surfaces of the powdery particles are coated and attached with the particulate silicone gel without gaps, or the non-particulate silicone gel are sparsely attached to the surfaces of the powdery particles, or the surfaces of the powder particles are coated and attached with the silicon gel in the filmy form without gaps. It may be that the above states are combined together.

For example, one kind of appropriate finely crosslinking reaction systems of the silicone to obtain the silicone gas as referred to in the present invention is accompanied with a condensation reaction between a silanol (≡Si—OH) group and a silicon hydride (≡Si—H), a condensation reaction between a silanol (≡Si—OH) group and a hydrolyzable or condensable silyl group, that is, ≡SiOR (alkoxy group), ≡Si—OC(O)CH3, ≡Si—NR2 and ≡Si—ON═CR2, a condensation reaction between silicon hydride and a hydrolyzable or condensable group, and a condensation reaction between two same or different hydrolyzable or condensable groups.

As one example of these finely crosslinking reaction system, a reaction is effected between a siloxane polymer having silanol groups and a crosslinkable compound having hydrolysable groups directly bonded to silicon atoms. As another example of this reaction system, a reaction is effected between a siloxane polymer having hydrolysable or condensable groups directly bonded to silicon atoms and a crosslinkable compound having a silanol group. As a further example of the above curing system, a reaction is effected between two siloxane polymers having hydrolysable or condensable groups directly bonded to silicon atoms. As a still further example of the above curing system, a reaction is effected between a siloxane polymer having hydrolysable or condensable groups directly bonded to silicon atoms and a siloxane polymer having a group with an active hydrogen atom, that is, a hydroxy group, a ureide group, a mercapto group or an amino group.

The most preferable kind of the finely crosslinking reaction system in the present invention is a condensation reaction between a hydroxysilyl group (≡SiOH) and an ethoxysilyl group (≡SiOCH2CH3), between a hydroxysilyl group (≡SiOH) and a methoxysilyl group (≡SiOCH3), between a hydroxysilyl group (≡SiOH) and a hydrosilyl group (≡SiH) or the like.

When the silicone gel is obtained by condensation reaction as a preferable finely crosslinking reaction system in a condensation reaction in the present invention, the diorganopolysiloxane with the reactive opposite ends shown in the above formula (1), the silane coupling agent shown in the above formula (2) and/or the reactive organopolysiloxane having at least three hydrolyzable groups per one molecule shown in the above formula (3) can be selected from among the following ones.

As the diorganopolysiloxane with the reactive opposite ends shown in the above formula (1), recitation is made of silicone modified at opposite ends with hydroxysilyl groups, or methoxy group, ethoxy groups, or amino groups, or hydroxysilyl groups at opposite ends. As generally available ones, recitation is made of silicones modified at opposite ends with hydroxysilyl groups such as X-21-5849, X-21-5841, KF-9701A (Shin-Etsu Chemical Co., Ltd.), FINISH WS 62M, CT601M, CT5000M, CT6000M (Asahi Kasei Waker Silicone Co., Ltd.), and silicones modified at opposite ends with amino groups, such as KF8010, X-22-161A, KF8008 (Shin-Etsu Chemical Co., Ltd.), etc. As a preferred diorganopolysiloxane with reactive opposite ends according to the present invention, a silicone (dimethiconol) modified at opposite ends with hydroxysilyl groups that produces water as a byproduct after hydrolysis and condensation reaction is recited.

As examples of the silane coupling agent shown by the above formula (2), recitation is made of dimethyldimethoxysilane, methyltrimethoxysilane, dimethyldiethoxysilane, methyltriethoxysilane, diphenyldiethoxysilane, phenyltriethoxysilane, 3-glycidoxypropyltriethoxysilane, 5,6-epoxyhexyltriethoxysilane, 2-(3,4-epoxycyclohexyl)ethyltriethoxysilane, 3-acryloxypropyltriethoxysilane, 3-methacryloxypropyltriethoxysilane, N-(2-aminoethyl)-3-amonopropyltriethoxysilane, 3-aminopropyltriethoxysilane, 3-mercaptopropylmethyldiethoxysilane, n-octyltriethoxysilane and the like. However, it is not limited to them, and a mixture of two or more kinds of them can be used depending upon a purpose.

As examples of the reactive organopolysiloxane having at least three hydrolyzable groups per one molecule shown in the above formula (3), recitation is made of α-trihydroxydimethylpolysiloxane, α-trialkoxypolydimethylsiloxane, α,ω-dialkoxypolydimethylsiloxane, α,ω-hexaalkoxypolydimethylsiloxane, dimethyl hydrogen polysiloxane, triethoxysilylethylpolydimethylsiloxyethyl dimethicon, triethoxysilylethylpolydimethylsiloxyethylhexyl dimethicone and the like. However, it is not limited to them, and a mixture of two or more kinds of them can be used depending upon a purpose.

The most preferable finely crosslinking reaction system in the present invention is a silicone gel in which the above crosslinking agent is reacted with the diorganopolysiloxane having the reactive opposite ends of the above formula (1) in the form of a water suspension or a water emulsion as a starting material. As a method for preparing a water emulsion of the diorganopolysiloxane having the above formula (1) with the reactive opposite ends, recitation is made of a method for effecting an emulsion polymerization by using a low-molecular cyclic siloxane as a starting material, or a method for mechanically emulsifying a system containing at least an oily diorganopolysiloxane having reactive opposite ends, a surface active agent and water by an emulsion mixing device. Any kind of mixing devices may be used to effect the emulsifying step. That is, a batch type mixer, a planetary type mixer, a continuous mixer such as a uniaxial or multi-axial screw extruder, a dynamic or static mixer, a colloid mill, a homogenizer or a sonolator or a combination may be used.

An emulsion may be produced by any publicly known method. For example, when a water emulsion of the diorganopolysiloxane having the reactive opposite ends is to be obtained by the mechanical emulsion, however, the method undergoes the limitation of the viscosity of the diorganosiloxane. The unit number of the diorganosiloxane is preferably in a range of 3 to 1,000. As a producing method, the emulsion can be obtained by mixing and emulsifying the diorganopolysiloxane having the reactive opposite ends, the surface active agent and water. The molecular weight of the obtained organopolysiloxane can be known by drying off the water of the emulsion and measuring the Mw of the remainder after the evaporation with GPC in terms of the PS conversion.

As another method, when the water emulsion of the diorganopolysiloxane having the reactive opposite ends is to be obtained by the emulsion polymerization, the water emulsion of the organopolysiloxane containing hydroxy groups bonded to silicon atoms of the opposite ends of the straight-chain molecule can be produced by adding a surface active agent and water to a lower-molecular cyclic cyclohexane or dimethiconol, emulsifying the mixture, and then performing the polymerization reaction through addition of an acid, and neutralizing a product mixture with addition of an alkaline. In this case, the number of diorganosiloxane units is preferably in a range of 3 to 1,000. The molecular weight of the obtained organopolysiloxane can be known by measuring the PS-converted Mw with the GPC in the same manner as mentioned before.

Meanwhile, as another method, a water emulsion of a partially finely crosslinked organopolysiloxane silicone containing hydroxyl groups bonded to silicone atoms of the opposite ends can be obtained by adding a fine amount of a crosslinking agent, a surface active agent and water to a lower-molecular cyclic siloxane, emulsifying them, then subjecting them to a polymerization reaction with the addition of an acid, and neutralizing them with the addition of an alkaline. In this case, the number of diorganosiloxane units is preferably in a range of 3 to 1,000.

The surface active agent to be used in emulsifying the water emulsion of the diorganopolysiloxane having the reactive opposite ends is not limited. For example, non-ionic surface active agents such as polyoxyethylene alkyl ether, polyoxyethylene polyoxypropyrene alkyl ether, polyoxyethylene alkylphenyl ether, polyethylene glycol fatty acid ester, sorbitan fatty acid ester, polyoxyethylene sorbitan fatty acid ester, polyoxyethylene sorbit fatty acid ester, glycerin fatty acid ester, polyoxyethylene glycerin fatty acid ester, polyglycerin fatty acid ester, propylene glycol fatty acid ester, polyoxyethylene propylene glycol fatty acid ester, polyoxyethylene castor oil, polyoxyethylene cured castor oil, polyoxyethylene cured castor oil fatty acid ester, polyoxyethylene phytostanol ether, polyoxyethylene phytosterol ether, polyoxyethylene cholestanol ether, polyoxyethylene cholesteryl ether, polyoxyethylene alkyl amine, alkylalkanol amide, sucrose fatty acid ester, methyl glycoside fatty acid ester, alkyl polyglycoside, straight chain- or branched polyoxyethylene-modified organopolysiloxane, straight chain- or branched polyoxyethylene polyoxypropyrene-modified organopolysiloxane, polyoxyethylene-alkyl co-modified organopolysiloxane, straight chain- or branched polyoxyethylenepolyoxypropyrene-alkyl co-modified organopolysiloxane, straight chain- or branched polyglycerin-modified organopolysiloxane, straight chain- or branched polyglycerin-alkyl co-modified organopolysiloxane, polyvinyl alcohol, polyvinyl pyrolidone, methyl cellulose and hydroxypropyl methyl cellulose; anionic surface active agent such as alkyl sulfate, polyoxyethylene alkyl ether sulfate, polyoxyethylene alkylphenyl ether sulfate, a sulfate of a fatty acid alkylolamide, alkylbenzene sulfonate, a polyoxyethylene alkylphenyl ether sulfonate, α-olefinsulfonate, an α-sulfo fatty acid ester salt, an alkyl naphthalene sulfonic acid, an alkyldiphenyl ether disulfonate, an alkane sulfonate, N-acyltaurinate, a dialkylsulfosuccinic acid, a monoalkylsulfosuccinate, a polyoxyethylene, a polyoxyethylenealkyl ether sulfosuccinate, a fatty acid salt, a polyoxyethylene alkyl ether carboxylate, an N-acylamino acid salt, a monoalkyl phosphate, a dialkyl phosphate, a polyoxyethylene alkyl ether phosphate, a carboxymethyl cellulose, a polyacrylate, a polystyrene sulfate, a naphthalene sulfonate formalin condensate, an aromatic sulfonate formalin condensate, a carboxyvinyl polymer, and a styrene oxyalkylene acid anhydride copolymer; cationic surface active agents such as an alkyltrimethyl ammonium salt, a dialkyldimethyl ammonium salt, a polyoxyethylene alkyl dimethyl ammonium salt, a dipolyoxyethylenealkylmethyl ammonium salt, a tripolyoxyethylenealkyl ammonium salt, an alkylbenzyldimethyl ammonium salt, an alkylpyridium salt, a monoalkylamine salt, a dialkylamine salt, a trialkylamine salt, a monoalkylamideamine salt and a cationic cellulose; amphionic surface active agents such as an alkyldimethylamine oxide, an alkyldimethylcarboxy betaine, an alkyl amide propylmethyl carboxybetaine, an alkylhydroxy sulfobetaine, an alkylcarboxymethyl hydroxyethylimidazolium betaine and the like. These surface active agents can be used singly or by appropriately combining two or more kinds thereof.

Preferable surface active agents are less irritating to skins, and not controlled substances by the PRTR law (Pollutant Release and Transfer Register). For example, Na or K salts and the like of a polyether-modified silicone, lauroyl glutamic acid, myristoyl glutamic acid, lauroyl asparaginic acid, myristoyl asparaginic acid, lauroyl alanine, lauroylmethyl taurine, myristoylmethyl taurine and the like are recited, and one or more kinds thereof can be mixed.

When a water emulsion of a diorganopolysiloxane with reactive opposite ends is used as a starting material to obtain a silicone gel referred to in the present invention, the surface active agent contained in the water emulsion is preferably as small as possible from the standpoint that it gives water repellency to the surface-treated powder and it remains due to adsorption in the powder. The mixing weight ratio (B)/(A)×100 is preferably less than 6.0 in which (A) is the amount of the organopolysiloxane with the reactive opposite ends and (B) is that of the surface active agent. If the weight ratio is 6.0 or more, the water repellency of the surface-treated powder may be lowered, or no light touch may be obtained.

The mixing ratio between the diorganopolysiloxane with the reactive opposite ends and the crosslinking agent and the number of the reactive groups are determined depending upon whether the silicone gel is obtained by the finely crosslinking reaction or not. In general, when the sum of the number of the reactive groups of the reactive diorganopolysiloxane and that of the reactive groups of the crosslinking is at least 5, a structural material in the form of a silicone elastomer is formed by a crosslinking reaction. If both of the molecular weight of the diorganopolysiloxane with the reactive opposite ends and that of the crosslinking agent are small, although not generally said because the obtained silicone polymer is a solid elastic body, the ratio of the diorganopolysiloxane with the reactive opposite ends and the crosslinking agent in the silicone gel according to the present invention is almost in a mixed ratio of 100/0.1 to 100/35 (wt %). If the amount of the crosslinking agent is less than 0.1 wt %, the product is a viscous silicone oil or gum, whereas if it is more than 35 wt %, the product is a silicone elastomer having elasticity to lower the water repellency of the surface-treated powder.

When the diorganopolysiloxane with the reactive opposite ends and the crosslinking agent are to be finely crosslinked, a catalyst to invoke the reaction may be added. As a preferably appropriate catalyst, an acidic substance or an alkaline substance is recited. The acidic substance is not particularly limited, and for example, organic acids such as lactic acid, citric acid, malic acid, succinic acid and the like, hydrochloric acid, sulfuric acid, phosphoric acid, aluminum chloride, zinc chloride, magnesium chloride, polyaluminum chloride, aluminum sulfate, zinc sulfate and the like can be used.

The alkaline substance is not particularly limited, and for example, alkaline metal hydroxides such as potassium hydroxide, sodium hydroxide, lithium hydroxide and the like; alkali earth metal hydroxides such as calcium hydroxide, magnesium hydroxide, barium hydroxide and the like; alkali metal carbonates such as potassium carbonate, sodium carbonate and the like; ammonia, triethanolamine and the like can be used.

In the present invention, as to the silicone gel, a compound composed mainly of a silicone having no rubbery elasticity is good. Generally, in case of the dimethylpolysiloxane, if the number of linear siloxane units is small, that is, if the molecular weight becomes small, the product is volatile. As the molecular weight increases, the product is from liquid, viscous liquid to gum. When a molecular crosslinking agent is added to the dimethylpolysiloxane chains having a linear molecular structure, the product changes from a gel, an elastic material to a resinous material with increase in the addition amount thereof.

The amount of the silicone gel to be used as a coating material for the surface treatment in the present invention differs depending upon the kind of the powder used and a coating method, and is not particularly limited. The ratio between the powder and the silicone gel as the surface treating agent is that the powder:the silicone gel is preferably 99.99:0.01 to 70:30, particularly preferably 99:1 to 90:10. When the ratio is in the above range, the surface-treated powder according to the present invention which is smooth and light touch with moist feeling and excellent adhesion to skin can be obtained.

The silicone gel referred to in the present invention is a polymer having a finely three-dimensional crosslinking structure of the diorganopolysiloxane without rubbery elasticity or rubber hardness. In order to specify the silicone gel in the present invention, a measuring method is available, in which the rubber hardness is measured by a durometer specified by ISO7619-1. As this measuring method, a measuring method with Durometer type AO which is capable of measuring the soft rubber hardness is available. A preferable measurement value of the silicone gel in the present invention is less than 10, more preferable less than 5, and further preferably 0.

Further, the silicone gel is used in the present invention, in which rheological properties of the silicone gel includes a complex modulus of 3,000 to 100,000 Pa, and a loss coefficient tan δ is 1.0 to 2.5 in measurement of a dynamic viscoelasticity under a distortion factor of 17% at 25° C. and a shear frequency of 4 Hz. More preferably, a complex modulus is 10,000 to 100,000 Pa, a loss coefficient (loss elasticity G"/storage elasticity G') tan δ is 1.0 to 2.0. If the complex modulus is less than 3,000 pa, the silicon gel exhibits the property of the silicone oil, which does not afford the usability in the present invention. If the complex modulus is more than 100,000, the product exhibits the elastic body, which tends to deteriorate the water repellency and adhesion to skin. If the loss coefficient tan δ is less than 1.0, the product exhibits the properties of the elastic body, which tends to deteriorate the water repellency and adherence to skin. If the loss coefficient tan δ is more than 2.5, the product exhibits the properties of the silicone oil, which does not afford the usability in the present invention. The reason why the shear frequency is set at 4 Hz is that it is in a range of a physically moving speed general to human beings, which is near to a speed at which a cosmetic composition is applied to skin. The rheological properties of the silicone gel in the present invention can be measured as follows. Measurement is carried out in an automatically measuring mode by a dynamic viscoelasticity measuring device: Rheosol-G3000 (manufactured by UBM Co., Ltd.) under a measuring jig: parallel plates in a diameter of 20 mm, a measuring frequency: 4 Hz, measuring temperature: 25±1.0° C., setting of measuring distortion: a distortion rate 17% being set, and a thickness of a measuring sample (gap): 1.0 mm.

As to a method of preparing samples in the measurement of the rubber hardness and the measurement of the dynamic viscoelasticity in the silicone gel, such samples can be obtained as residues through evaporation of water under heating after the diorganopolysiloxane having the reactive opposite ends is emulsified in ion-exchanged water with a surface active agent, a crosslinking agent is added thereto and pH of the mixture is adjusted to basic.

[2] Method for Producing Silicone Gel Surface-Treated Powders

The cosmetic powder coated with the silicone gel according to the present invention can be produced by simply mixing and treating the cosmetic powder with the silicone gel by a mixer or the like. Since the silicone gel firmly agglomerates the powder particles together, it is preferable that mixing is carried out by using an organic solvent with a lower surface tension in combination from the standpoint of the water repellency, usability and adhesion to the skins. As a more preferable method for producing the silicone gel-treated powder according to the present invention, after the silicone gel is deposited on the surfaces of the powder particles in the presence of the cosmetic powder by an in-situ method, the treated powder can be obtained by fixing the silicone gel onto the surfaces of the particles under heating. As a further preferable method, a water emulsion of the organopolysiloxane with the reactive opposite ends is used as a starting material, and the silicone gel is fixed by the above in-situ method. This method enhances the uniform attachment and coating of the silicone gel onto the surfaces of the powder particles, so that water repellency is improved and good and lighter usability can be afforded. Thereby, the excellent silicone gel surface-treated cosmetic powder can be obtained due to the adherence to the skins.

According to the method for producing the cosmetic powder surface-treated with the silicone gel in the present invention, in a step in which the diorganopolysiloxane of the above (1) having the reactive opposite ends and the compound in the above (2) or the above (3) are separately or simultaneously added in a state that a mixing state of the water soluble solvent and the powder for cosmetics is in a capillary or slurry state, at least a part of the mixture is hydrolyzed and condensed, and thereafter the surface-treated powder is obtained by heating at an internal temperature of 100 to 180° C. for 3 hours or more. More specifically, although different depending upon the particle diameters, the specific surface area and the absorbed water of the powder, the water soluble component is preferably in an amount of 3 to 1500 mass parts, more preferably 10 to 800 mass parts relative to 100 mass parts of the powder for cosmetics. If the water soluble component is less than 3 mass parts, the mixture is not in the capillary state but in a dry mixed state, so that the powder particles are agglomerated to deteriorate the usability. If the water soluble component is unfavorably more than 1500 mass parts, the productivity of the surface-treated powder is deteriorated to increase the production cost.

The mixing state of the powder and the liquid as referred to in the present invention means that although as a packed state among solid, liquid and gas, there are (a) a dry state in which a solid phase and a gas phase continue, and almost no liquid phase exists; (b) a pendular state in which the solid phase and the gas phase are continuous, and the liquid phase is discontinuous; (c) a funicular state in which the solid phase, the gas phase and the liquid phase are continuous: (d) a capillary state in which the solid state is discontinuous, while the liquid is continuous but does not flow; and (e) a slurry state in which the solid phase is discontinuous and the liquid is continuous and flows, and the hydrolysis and the condensation reaction is preferably carried out in the state (d) or (e) among them, while the mixture is being mixed, kneaded or stirred.

The water-soluble solvent refers to any of water, ethanol and ispropyl alcohol (IPA) and a mixed solvent thereof. Water is preferable as the water-soluble solvent from the standpoint of the environment and the cost, and ethanol or IPA can be used as a washing solvent when a compound produced as a byproduct in a reaction process, the surface active agent and the like are to be removed.

As the producing method in the capillary state, for example, after the cosmetic powder, the water-soluble solvent and the diorganopolysiloxane having the reactive opposite ends are well kneaded in a kneader, the crosslinking agent is gradually added thereto under kneading, and if necessary, an acidic material or an alkaline material is added as reaction catalyst, followed by further kneading for a given time. After the kneaded mixture is taken out, the mixture is heated at a temperature of 100 to 180° C. in a hot gas dryer for 3 hours or more with an internal temperature being a preset temperature, and then cooled and crushed to obtain the powder surface-treated with the silicone gel. Although dimethiconol may be in an oily form or a water-emulsion form at that time, the water emulsion is preferably used from the standpoint of the water repellency.

As a producing method in the slurry state, for example, the cosmetic powder is fed into a water soluble solvent, which is dispersed in a stirrer. After a water emulsion of the diorganopolysiloxane with the reactive opposite ends is gradually added under stirring and the mixture becomes homogeneous, a crosslinking agent is gradually added, which is further stirred, and if necessary, an acidic material or an alkaline material is added thereto as a reaction catalyst, followed by stirring for a given time period. As the condensation reaction proceeds, the slurry liquid becomes viscous, so that the mixture is stirred for a given time. The liquid is removed from the resultant by filtration or a centrifugal separator, which is washed and liquid-removed if necessary. After the resulting cake is heated at a temperature of 100 to 180° C. by a hot gas dryer for 3 hours or more with an internal temperature being at a preset temperature, the resultant is cooled and crushed to obtain the powder treated with the silicone gel. Separation of the solid and the liquid can be carried out at this time by heating under ordinary pressure or reduced pressure. More specifically, a method in which water is removed by keeping still the dispersion liquid under heating, a method in which water is removed by flowing the dispersion liquid under stirring and heating, a method in which the dispersion liquid is sprayed and dispersed in a hot gas stream as in a flush dryer, a spray dryer or the like, and a method utilizing a fluidizing heat medium are recited, for example.

In the producing method in the capillary state or the slurry state, the adding order of the diorganopolysiloxane with the reactive opposite ends, the crosslinking agent and the reaction catalyst may be set such that the effects of the present invention may be obtained to a largest extent depending upon the kind of the powder. They may be separately or simultaneously added.

As to the kneading and the stirring in the above producing methods, strong kneading and stirring are preferable, because the powder particles can be homogeneously surface-treated, and a kneader, a biaxial kneader, a disperser mixer, a homomixer and the like are recited.

The temperature in the surface treatment is preferably 5 to 60° C., and more preferably 15 to 30° C. If this temperature is less than 5° C., the hydrolysis and condensation reaction is less likely to proceed, so that the intended effects cannot be obtained, whereas if the temperature is more than 60° C., the obtained particles are strongly agglomerated, so that the usability is deteriorated.

The dried powder may be crushed or classified by a crushing device such as a pin mill, a hammer mill, a jet mill, a ball mill or the like, depending upon the agglomerated state of the powder particles.

[3] Solid Powdery Cosmetic Composition Containing Powder Surface-Treated with Silicone Gel The solid powdery cosmetic composition according to the present invention is obtained by the above-mentioned methods, and recitation is made of makeup cosmetics such as foundation, white powder, rouge, lipstick, eye shadow, eyeliner, eye blow, concealer, etc. Meanwhile, the solid powdery cosmetic compositions according to the present invention are molded in various three-dimensional shapes such as a doom shape, a spherical shape, a semi-spherical shape, a conical shape, a pyramid shape, a diamond cut shape, a stick shape, etc. The compounding ratio of the powder surface-treated with the silicone gel according to the present invention is not particularly limited, and is appropriately selected in a range of 0.1 to 100.0 mass % relative to the entire cosmetic composition, depending upon each preparation. Various ingredients usually used in the cosmetic compositions are mixed into the above cosmetic compositions so long as the effects of the present invention are not deteriorated. As such components, for example, an oily agent, a powder, a surface active agent, a water-soluble or water-swellable macromolecular compound, a UV absorbing agent, a moisturizing agent, an oil soluble gelatinizing agent, an antibacterial and antiseptic agent, salts, an antioxidant, an beauty skin ingredient (a beauty skin agent, a cell stimulant, a skin roughness improver, a blood circulation promoter, a skin astringent, an antiseborrheic agent, etc.), vitamins, amino acids, a antiperspirant, alcohols, a skin film forming agent, an anti-inflammatory agent, a refreshing agent, nucleic acids, hormones, a clathrate compound, a pH control agent, a chelate agent and other additives may be incorporated. They can be used singly or two or more kinds of them can be used in appropriately combined manners.

EXAMPLES

In the following, the present invention will be explained by showing examples and comparative examples, but the invention is not limited to the following examples.

A dimethiconol oil (α, ω-dihydroxypolydimethylsiloxane having a viscosity of 30 mPa·s) was prepared as a diorganopolysiloxane having reactive opposite ends. A water emulsion of dimethiconol was prepared by the following method.

Production Example 1 for a Water Emulsion of Dimethiconol by Emulsification Polymerization Dimethiconol having the above viscosity of 30 mPa·s, 500 g, was charged into a polyethylene beaker with a volume of 2 liters, and 22.5 g of sodium lauroylmethyl taurate and 50 g of ion-exchanged water were gradually dropped thereto under stirring with a homomixer at 5,000 rpm, thereby effecting phase inversion. After increasing the viscosity, the stirring speed was increased to 7,000 rpm, followed by stirring for 15 minutes, and the mixture was diluted with the addition of 450 g of ion-exchanged water. Thereafter, the resultant was emulsified and dispersed once in a portable press homogenizer (manufactured by APV Gaulin) at 70 MPa, thereby obtaining an emulsion. After citric acid, 4.5 g, as a condensation catalyst was fed to and stirred with the thus obtained emulsion, a condensing polymerization reaction was effected for 10 hours. Then, a water emulsion was obtained by adjusting the resultant to pH 7 with the addition of 10% sodium carbonate. A solid component was obtained by evaporating off water by drying the water emulsion at 105° C. for 3 hours, and its molecular weight was determined to be 150,000 as PS conversion by GPC. The solid component was 49.5%.

Production Example 2 for a Water Emulsion of Dimethiconol by Emulsification Polymerization Octamethylcyclotetrasiloxane, 450 g, 500 g of ion-exchanged water and 6.75 g of sodium lauroylmethyl taurate and were charged into a polyethylene beaker with a volume of 2 liters, and the mixture was preliminarily stirred with a homomixer at 2,000 rpm. Thereafter, 4 g of citric acid was added to the resultant, which was heated to 70° C., and subjected to emulsion polymerization at 5,000 rpm in a homomixer for 24 hours. A water emulsion of dimethiconol having a high molecular weight was obtained by emulsifying and dispersing the resultant by the portable press homogenizer (manufactured by APV Gaulin) once at 50 MPa. Thereafter, the resultant was adjusted to pH7 by adding 10% sodium carbonate, thereby obtaining a water emulsion. A solid component was obtained by evaporating off water by drying the water emulsion at 105° C. for 3 hours, and its molecular weight was determined to be 10,000 as PS conversion by GPC. The solid component was 46.5%.

The following compositions were prepared as crosslinking agents for dimethiconol. 1. Product name: KBE-903 (aminopropyltriethoxysilane: Shin-Etsu Chemical Co., Ltd.), 2. Product name: KBE-13 (methyltriethoxysilane: Shin-Etsu Chemical Co., Ltd.), 3. Product name: KF-9901 (methyl hydrogen polysiloxane (the number of Si—O units being about 40, Si-2CH3/Si—CH3H ratio=1/1: Shin-Etsu Chemical Co., Ltd.). Finely crosslinked reaction products of silicone were obtained with mixtures shown in Table 1, and mixing ratios at which silicone gels were obtained were confirmed. A method for preparing the reaction product of silicone was shown below.

(Preparation of a Finely Crosslinked Reaction Product of Silicone)

In a 300 ml vessel made of PP, 0.1 g of sodium lauroylmethyl taurate was dissolved into 100 g of ion-exchanged water, log of diorganopolysiloxane oil (A) with reactive opposite ends was gradually added thereto in a homomixer under stirring at 6000 rpm. The resultant was maintained stirred for 10 minutes and emulsified at a room temperature, thereby obtaining a water emulsion. Into this emulsion was added the crosslinking agent (B) 25 wt % IPA solution under stirring by a stirrer. Then, if necessary, the resultant was adjusted to pH10.5 with a 1N-NaOH aqueous solution, which was stirred for 15 minutes and moved in an aluminum plate. A silicone reaction product was obtained by evaporating water at 105° C./24 h. In case that the diorganopolysiloxane with the reactive opposite ends is a water emulsion, the water emulsion having 10 g of a solid component was charged, and subjected to the same steps as mentioned above with the ion-exchanged water such that the content of the water is 100 g. The mixing weight ratio (A)/(B) between the diorganopolysiloxane with the reactive opposite ends (A) and the crosslinking agent (B) was set at any of 100/10, 7/1 or 3/1.

(Measuring Condition with a Durometer AO)

A silicone reaction product was charged into a styrol square case (vertical 36 mm×lateral 36 mm×height 14 mm) such that it protruded slightly from a face of the case, and the surface of the reaction product was flattened as a test surface. A press plate of a durometer was set over the test surface by 20 mm, and a scale of a needle was read by pressing the press plate onto the test piece in the state that the surface of the test face and the press plate were being maintained in parallel. This operation was carried out 5 times, and a measured value was obtained by the averaged value.

(Measuring Condition of a Complex Modulus and Tan δ in a Dynamic Viscoelasticity Measurement)

Under conditions shown below, G' (storage modulus) and G" (loss modulus) were determined, and a complex modulus and tan δ were determined.

[Formula 1]

$$\text{Complex modulus} = \sqrt{G'^2 \times G''^2} \quad (1)$$

$$\tan \delta = G''/G' \quad (2)$$

Viscoelasticity measuring device: Rheosol-G3000 (manufactured by UBM)
Measuring jig: Parallel plate in 20 mm diameter
Measuring frequency: 4 Hz
Measuring temperature: 25±1.0° C.
Setting of distortion in measurement: A distortion rate was set at 17%, and measurement was effected in an automatic measuring mode.
Thickness (gap) of a sample to be measured: 1.0 mm

TABLE 1

| Comp. No. | Dimechikonol (A) | Crosslinking agent (B) | (A)/(B) wt % ratio | Duometer AO value | Complex modulus (Pa) | tan δ |
|---|---|---|---|---|---|---|
| 1 | Viscosity 30 mPa·s | KBE-903 | 100/10 | NA | 23.217 | 1.051 |
| 2 | Viscosity 30 mPa·s | KF9901 | 3/1 | NA | 11.267 | 1.668 |
| 3 | Water emulsion in Producing Example 1 | KF9901 | 7/1 | NA | 9.351 | 2.376 |
| 4 | Water emulsion in Producing Example 1 | KBE-13 | 3/1 | NA | 72.675 | 1.416 |
| 5 | Water emulsion in Producing Example 2 | KBE-903 | 100/10 | NA | 17.464 | 1.353 |
| 6 | Water emulsion in Producing Example 2 | KF9901 | 3/1 | NA | 10.180 | 1.934 |
| 7 | Water emulsion in Producing Example 2 | KBE-13 | 7/1 | NA | 35.882 | 1.674 |

Any of the silicone compositions exhibited physical properties of the silicone gels.

Production of a Cosmetic Powder Surface-Treated with a Silicone Gel

Example 1

Ratio of Dimethiconol/Crosslinking Agent=100/10 wt %

Into a fit powder FK-300S (manufactured by Yamaguchi Unmo Industries, Ltd.), 1 kg, was charged into a universal mixer, and 550 g of water and a mixed liquid of IPA/dimethiconol having a viscosity of 30 mPa·s in a ratio of 60 g/35 g were added thereto, followed by mixing and stirring for 15 minutes, thereby obtaining a soft paste of the powdery particles (in a capillary state). A 5 mass % aqueous solution of KBE-903, 70 g, was added as a crosslinking agent to the resultant, followed by mixing and stirring for 15 minutes. The soft paste was taken out, which was dried at 120° C. for 16 hours by a drier. Insertion of a temperature sensor into the paste at this time revealed that the internal temperature was 115° C. or more, while heated for 5 hours. Talc surface-treated with the silicone gel was obtained by pulverizing the dried cake with a pulverizer.

Example 2

Ratio of Dimethiconol/Crosslinking Agent=100/10 wt %

Into a PE-made vessel with a volume of 20 liters were charged 7 L of water and 1 kg of Eight pearl 300S (manufactured by Kakuhachi Uorinpaku Co, ltd.), which was dispersed (in a slurry state) at 2000 rpm for 5 minutes in a disperser mixer (Prime Mix Co., Ltd.; AM-40). Then, 103 g of the water emulsion of dimethiconol (Producing Example 2) was added thereinto, which was stirred at 2500 rpm for 5 minutes. Thereafter, 96 g of a 5 wt % aqueous solution of KBE-903 was added as a crosslinking agent. After the resultant was adjusted to pH10.3 with a 1N-NaOH aqueous solution, the resultant was reacted under stirring at 3000 rpm for 30 minutes. After the resultant was filtered with a centrifugal dewatering machine and washed with 7 L of water, the dewatered cake was dried at 120° C. for 16 hours in a dryer. At that time, when an internal temperature was recorded in a state that a temperature sensor was inserted into the cake, it was revealed that the cake was heated at the internal temperature of 115° C. or more for 7 hours. Sericite surface-treated with silicone gel was obtained by pulverizing the dried cake with the pulverizer.

Example 3

Ratio of Dimethiconol/Crosslinking Agent=4/1 wt %

A synthesized mica PDM-40L (manufactured by Topy Industries Ltd.), 1 kg, was charged into the universal mixer, and a water emulsion of 450 g of water and 213 g of dimethiconol (Producing Example 1) was added thereinto, and a soft paste (in a capillary state) was obtained by stirring for 15 minutes. KF-9901, 10.5 g, was added as a crosslinking agent to the resultant, and 4 ml of a 28% ammonia aqueous solution was added thereto, followed by mixing and stirring for 15 minutes. The resultant was taken out, and was dried at 140° C. for 16 hours in a dryer. At that time, when an internal temperature was recorded in a state that a temperature sensor was inserted into the paste, it was revealed that the paste was heated at the internal temperature of 135° C. or more for 8 hours. A synthetic mica surface-treated with silicone gel was obtained by pulverizing the dried cake with the pulverizer.

Example 4

Ratio of Dimethiconol/Crosslinking Agent=100/10 wt %

Water, 7 L, and 1 kg of mica titanium Timiron Splendid Blue (manufactured by Merck Co., Ltd.) were charged into a PE-made vessel with a volume 20 liters, followed by dispersing (in a slurry state) at 3000 rpm for 5 minutes in a disperser mixer (Prime Mix Co., Ltd.; AM-40). After 117 g of the water emulsion of the dimethiconol (Producing Example 1) was added to the resultant, followed by stirring at 3000 rpm for 5 minutes. Thereafter, 116 g of a 5 mass % aqueous solution of KBE-903 was added to the resultant, which was stirred at 3000 rpm for 15 minutes. After the resultant was filtered with the centrifugal dewatering device and washed with 7 L of water, the dewatered cake was dried at 120° C. for 16 hours in the dryer. At that time, when an internal temperature was recorded in a state that a temperature sensor was inserted into the past, it was revealed that the mixture was heated at the internal temperature of 115° C. or more for 6 hours. The mica titanium surface-treated with the silicone gel was obtained by pulverizing the dried cake with the pulverizer.

Example 5

Ratio of Dimethiconol/Crosslinking Agent=100/10 wt %

Mica titanium surface-treated with the silicone gel was obtained in the same manner as in Example 4 except that the mica titanium was replaced by Timica Extra Large Sparkle (manufactured by BASF Co., Ltd.)

Comparative Examples 1 to 5

Powders Surface-Treated with Methyl Hydrogen Polysiloxane

Into a 10 L super mixer was charged each of 1 kg of the powders used in Examples 1 to 5, and a mixture of 30 g of methyl hydrogen polysiloxane, KF99P (manufactured by Shin-Etsu Chemical Co., Ltd.) and 50 g of 99.5% ethyl alcohol was added thereto, followed by stirring at room temperature for 30 minutes. The mixture was further heated up to 150° C. and held for 5 hours. Each powder treated with methyl hydrogen polysiloxane was obtained by pulverizing with the pulverizer.

Comparative Examples 6 to 10

Powders Surface-Treated with Dimethylpolysiloxane

Into a 10 L super mixer was charged each of 1 kg of the powders used in Examples 1 to 5, and a mixture of 30 g of dimethylpolysiloxane having a triethoxy group at one end (n number 50) and 50 g of hexane was added thereto under vigorously stirring, followed by stirring at room temperature for 30 minutes, while N2 gas was being flown into the mixer. The mixture was further heated up to 150° C. and held for 5 hours. Each powder treated with dimethylpolysiloxane was obtained by pulverizing with the pulverizer.

(1) Measurement of the Surface Hardness of a Pressed Powder

The surface-treated powder obtained in each of Examples and Comparative Examples was press molded in a gold dish under pressure of 0.2 and 0.4 MPa without addition of a binder thereto, and measurements were made at 5 spots of a molded surface with an Olsen hardness meter, and the average value was taken as a surface hardness. The larger the value, the softer is the molded surface.

(2) Impact Resistance Evaluations

The surface-treated powder obtained in each of Examples and Comparative Examples was press molded in a gold dish under pressure of 0.2 and 0.4 MPa without addition of a binder thereto, which was set in a cosmetic compact vessel as a sample. The sample was dropped on a concrete in a horizontal state from a height of 50 cm, and impact resistance was evaluated by the number of times at which the molded product was broken.

⊚: Cracked at 10 times or more

○: Cracked at 8 to 9 times

Δ: Cracked at 6 to 7 times x: Cracked at 5 times or less (3) Removability with an Applicator The surface-treated powder obtained in each of Examples and Comparative Examples was press molded in a gold dish under pressure of 0.2 and 0.4 MPa without addition of a binder thereto, which was set in a cosmetic compact vessel as a sample. Rubbing removal degrees on a molded surface of the sample with sponge puffs were evaluated by 10 expert panelers as follows.

○: Appropriately removed

Δ: Removed too much x: Cracked

Results were shown in Table 2.

TABLE 2

| Sample | Molding pressure (MPa) | Olsen hardness | Impact resistance | Removal degree |
|---|---|---|---|---|
| Treated powder of Exam. 1 | 0.2 | 96 | ○ | ○ |
| | 0.4 | 78 | ⊚ | ○ |
| Treated powder of Com. Exam. 1 | 0.2 | Cracked in measurement | Δ | Δ |
| | 0.4 | Cracked in measurement | X | X |
| Treated powder of Com. Exam. 6 | 0.2 | Molding was impossible | X | X |
| | 0.4 | Molding was impossible | X | X |
| Treated powder of Exam. 2 | 0.2 | 105 | ⊚ | ○ |
| | 0.4 | 94 | ⊚ | ○ |
| Treated powder of Com. Exam. 2 | 0.2 | 109 | X | X |
| | 0.4 | 98 | X | X |
| Treated powder of Com. Exam. 7 | 0.2 | Molding was impossible | X | X |
| | 0.4 | Molding was impossible | Δ | X |
| Treated powder of Exam. 3 | 0.2 | 85 | ○ | ○ |
| | 0.4 | 76 | ⊚ | ○ |
| Treated powder of Com. Exam. 3 | 0.2 | Cracked in measurement | X | X |
| | 0.4 | Cracked in measurement | X | X |
| Treated powder of Com. Exam. 8 | 0.2 | Molding was impossible | X | X |
| | 0.4 | Molding was impossible | X | X |

As is seen from the above results, the powders surface-treated with the silicone gels according to the present invention have excellent impact resistance and good removal degrees. Particularly, although Example 2 and Comparative Example 2 had the same surface hardness, the powder surface-treated with the silicone gel according to the present invention has excellent impact resistance and removal degree.

Next, compounding examples of the solid powdery cosmetic compositions according to the present invention in various shapes will be explained as Examples.

Example 6 and Comparative Examples 11 and 12

Powder Foundation (Method)

An oily ingredient was added to powdery ingredients in formulations shown in Table 4, and the resultant was mixed for a given time period with a Henschel mixer (Mitsui Mining Co., Ltd.), and thereafter pulverized with a pulverizer as a hammer type pulverizer, which was filled in an inner dish. A powder foundation was obtained by press molding the resultant.

(Evaluations of Usability)

The evaluations were made into 5 stages with marks according to the following absolute evaluations by 10 persons of an expert evaluation panel. As to each of the samples, the average value was calculated from the total marks of all the persons of the panel, and judgment was made according to the following four stages.

(Absolute Evaluation)

(Marks): (Evaluations)
5: Very good
4: Good
3: Medium
2: Slightly bad
1: Bad

TABLE 3

(Judgment standard)

| Average value of marks | Judgment | |
|---|---|---|
| 4. 5 or more | Very good | ⊚ |
| 3. not less than 4.5 and less than 5 | Good | ○ |
| 2. not less than 3.5 and less than 4.5 | Slightly bad | Δ |
| 1. less than 3.5 | Bad | X |

(Evaluations of Impact Resistance)

The cosmetic composition obtained in each of Examples and Comparative Examples was set in a vessel, and the resulting sample was dropped on a concrete in a horizontal state from a height of 50 cm, and impact resistance was evaluated by the number of times at which the molded product was broken.

⊚: Cracked at 10 times or more
○: Cracked at 8 to 9 times
Δ: Cracked at 6 to 7 times
x: Cracked at 5 times or less

TABLE 4

| | Example 6 | Com. Example 11 | Com. Example 12 |
|---|---|---|---|
| Treated talc of Example 1 | 30.0 | — | — |
| Treated talc of Com. Example 1 | — | 30.0 | — |
| Treated talc of Com. Example 6 | — | — | 30.0 |
| Sericite of Example 2 | to 100.0 | — | — |
| Sericite of Com. Example 3 | — | to 100.0 | — |
| Sericite of Com. Example 7 | — | — | to 100.0 |
| Synthetic mica of Example 3 | 10.0 | — | — |
| Synthetic mica of Com. Example 3 | — | 10.0 | — |
| Synthetic mica of Com. Example 8 | — | — | 10.0 |
| Spherical powder of silicone elastomer*1 | 6.0 | 6.0 | 6.0 |

TABLE 4-continued

| | Example 6 | Com. Example 11 | Com. Example 12 |
|---|---|---|---|
| Nylon powder | 5.0 | 5.0 | 5.0 |
| Aluminum stearate-treated finely particular titanium oxide | 5.0 | 5.0 | 5.0 |
| Zinc oxide | 2.0 | 2.0 | 2.0 |
| Hydrophobic haze silica*2 | 1.0 | 1.0 | 1.0 |
| Fluorine-treated titanium oxide | 10.0 | 10.0 | 10.0 |
| Fluorine-treated colcothar | 0.8 | 0.8 | 0.8 |
| Fluorine-treated yellow iron oxide | 2.0 | 2.0 | 2.0 |
| uorine-treated black iron oxide | 0.1 | 0.1 | 0.1 |
| Dimethyl polysiloxane (6 mPa · s) | 2.0 | 2.0 | 2.0 |
| Octyl methoxycinnamate | 3.0 | 3.0 | 3.0 |
| Squalane | 2.0 | 2.0 | 2.0 |
| Triglyceryl 2-Ethylhexanoate | 2.0 | 2.0 | 2.0 |
| Sorbitan sesqui isostearate | 1.0 | 1.0 | 1.0 |
| Antioxidant | Appropriate amount | Appropriate amount | Appropriate amount |
| Perfume | Appropriate amount | Appropriate amount | Appropriate amount |
| Impact resistance | ⊚ | Δ | X |
| Usability | ⊚ | X | ○ |

*1 Torefil E-506S (manufactured by Dow Corning Toray Co., Ltd.)
*2 Aerosil R972 (Nippon Aerosil Co., Ltd.)

As seen from the results in Table 4, the powder foundation in which the product according to the present invention was compounded has good impact resistance and removability with the applicator and excellent usability, as compared with Comparative Examples.

Example 7 and Comparative Examples 13 and 14

Face Powders (Method)

Ingredients shown in Table 5 are homogeneously mixed except for a light liquid isoparaffin. The light liquid paraffin was added thereto, followed by uniform mixing. After the mixed slurry was filled in a vessel, a face powder was obtained by drying it under condition of 70° C. for 24 hours.

TABLE 5

| | Example 7 | Comparative Example 13 | Comparative Example 14 |
|---|---|---|---|
| Talc | to 100.0 | to 100.0 | to 100.0 |
| Mica | 10.0 | 10.0 | 10.0 |
| Sericite of Example 2 | 15.0 | — | — |
| Sericite of Comparative Example 3 | — | 15.0 | — |
| Sericite of Comparative Example 7 | — | — | 15.0 |
| Mica titanium of Example 4 | 2.0 | — | — |
| Mica titanium of Comparative Example 4 | — | 2.0 | — |
| Mica titanium of Comparative Example 9 | — | — | 2.0 |
| PMMA | 5.0 | 5.0 | 5.0 |
| Titanium oxide | 5.5 | 5.5 | 5.5 |
| Colcothar | 0.5 | 0.5 | 0.5 |
| Yellow iron oxide | 1.5 | 1.5 | 1.5 |
| Black iron oxide | 0.3 | 0.3 | 0.3 |
| Ultramarine | 0.3 | 0.3 | 0.3 |
| Paraben | 0.1 | 0.1 | 0.1 |
| Perfume | 0.2 | 0.2 | 0.2 |
| Silicone resin*3 | 1.5 | 1.5 | 1.5 |
| Light fluid paraffin | 60.0 | 60.0 | 60.0 |

TABLE 5-continued

|  | Example 7 | Comparative Example 13 | Comparative Example 14 |
|---|---|---|---|
| Impact resistance | ◎ | Δ | X |
| Usability | ◎ | Δ | ○ |

*3SILFORM FLEXIBLE RESIN (Manufactured by Momentive Co., Ltd.)

As seen from the results in Table 5, the face powder in which the product according to the present invention was compounded has good impact resistance and removability with the applicator and excellent usability, as compared with Comparative Examples.

Example 8 and Comparative Examples 15 and 16

Cake Eye Shadows (Method)

Ingredients shown in Table 6 are homogeneously mixed except water/ethanol solution. The water/ethanol solution is added thereto, followed by homogeneous mixing. After the mixed slurry was filled in a vessel, a cake eye shadow was obtained by drying it under condition of 70° C. for 12 hours.

TABLE 6

|  | Example 8 | Comparative Example 15 | Comparative Example 16 |
|---|---|---|---|
| Treated synthetic talc of Example 3 | 30.0 | — | — |
| Treated synthetic talc of Comparative Example 3 | — | 30.0 | — |
| Treated synthetic talc of Comparative Example 8 | — | — | 30.0 |
| Mica titanium of Example 4 | 25.0 | — | — |
| Mica titanium of Comparative Example 4 | — | 25.0 | — |
| Mica titanium of Comparative Example 9 | — | — | 25.0 |
| Mica titanium of Example 5 | 15.0 | — | — |
| Mica titanium of Comparative Example 5 | — | 15.0 | — |
| Mica titanium of Comparative Example 10 | — | — | 15.0 |
| Talc | to 100.0 | to 100.0 | to 100.0 |
| Nylon powder | 5.0 | 5.0 | 5.0 |
| Red 202 | 0.1 | 0.1 | 0.1 |
| Paraben | 0.1 | 0.1 | 0.1 |
| Perfume | 0.2 | 0.2 | 0.2 |
| Spherical powder of silicone elastomer*4 | 4.0 | 4.0 | 4.0 |
| Mixed solution of water/ethanol (25%) | 50.0 | 50.0 | 50.0 |
| Impact resistance | ◎ | Δ | X |
| Usability | ◎ | Δ | ○ |

*4KSP-300 (Manufactured by Shin-Etsu Chemical Co., Ltd.)

As seen from the results in Table 6, the face powder in which the product according to the present invention was compounded has good impact resistance and removability with the applicator and excellent usability, as compared with Comparative Examples.

Example 9 and Comparative Examples 17 and 18

Cheek Rouge (Method)

An oily ingredient was added to the powdery ingredients in formulations shown in Table 7, and the resultant was mixed for a given time period with the Henschel mixer (Mitsui Mining Co., Ltd.), and thereafter pulverized with a pulverizer as a hammer type pulverizer, which was filled in an inner dish. A cheek rouge was obtained by press molding the resultant.

TABLE 7

|  | Example 9 | Comparative Example 17 | Comparative Example 18 |
|---|---|---|---|
| Talc | to 100.0 | to 100.0 | to 100.0 |
| Sericite | 12.0 | 12.0 | 12.0 |
| Spherical silicic anhydride | 5.0 | 5.0 | 5.0 |
| Hydrocarbon wax powder | 1.5 | 1.5 | 1.5 |
| Red No. 226 | 0.8 | 0.8 | 0.8 |
| Mica titanium of Example 4 | 35.0 | — | — |
| Mica titanium of Comparative Example 4 | — | 35.0 | — |
| Mica titanium of Comparative Example 9 | — | — | 35.0 |
| Titanium oxide-coated glass powder | 3.0 | 3.0 | 3.0 |
| Octyl methoxycinnamate | 2.5 | 2.5 | 2.5 |
| Isononyl isononanoate | 3.0 | 3.0 | 3.0 |
| Decaglyceryl fatty acid ester | 0.5 | 0.5 | 0.5 |
| Paraben | 0.1 | 0.1 | 0.1 |
| Antioxidant | Appropriate amount | Appropriate amount | Appropriate amount |
| Perfume | Appropriate amount | Appropriate amount | Appropriate amount |
| Impact resistance | ◎ | X | X |
| Usability | ◎ | X | ○ |

(Measuring Condition with a Durometer AO)

A silicone reaction product was charged into a styrol square case (vertical 36 mm×lateral 36 mm×height 14 mm) such that it protruded slightly from a face of the case, and the surface of the reaction product was flattened as a test surface. A press plate of a durometer was set over the test surface by 20 mm, and a scale of a needle was read by pressing the press plate onto the test piece in the state that the surface of the test face and the press plate were being maintained in parallel. This operation was carried out 5 times, and a measured value was obtained by the averaged value. Note that when the needle was not moved in the measurement, it was called NA (Not Applicable).

(Measuring Condition of a Complex Modulus and Tan δ in a Dynamic Viscoelasticity Measurement)

Under conditions shown below, G' (storage modulus) and G" (loss modulus) were determined, and a complex modulus and tan δ were determined.

[Formula 1]

$$\text{Complex modulus} = \sqrt{G'^2 + G''^2} \quad (1)$$

$$\tan \delta = G''/G' \quad (2)$$

Viscoelasticity measuring device: Rheosol-G3000 (manufactured by UBM)
Measuring jig: Parallel plate in 20 mm diameter
Measuring frequency: 4 Hz
Measuring temperature: 25±1.0° C.
Setting of distortion in measurement: A distortion rate was set at 17%, and measurement was effected in an automatic measuring mode.
Thickness (gap) of a sample to be measured: 1.0 mm

What is claimed is:

1. A plate-like powder for a cosmetic composition, said powder having particles with an average particle diameter in a range of from 0.01 to 700 μm as a starting material that are surface-treated with a silicone gel by forming the silicone gel thereon in an in-situ method that comprises hydrolyzing and condensing an organopolysiloxane containing at least (i) a diorganopolysiloxane with reactive opposite ends expressed by the following formula (1) and (ii) at least one crosslinking agent selected from the group consisting of (a) a silane coupling agent having the following formula (2) and at least two hydrolyzable groups per one molecule and (b) a reactive organopolysiloxane of the following formula (3):

(Chemical formula 1)

$$R^1R^2{}_2SiO-(R^2{}_2SiO)_L-SiR^1R^2{}_2 \quad (1)$$

wherein $R^1$ is a hydrolyzable group selected from the group consisting of a hydroxyl group, an amino group, an acetoxy group, an alkoxy group or a hydrogen atom, $R^2$ is a non-substituted or substituted $C_1$-$C_{20}$ monovalent hydrocarbon group, and L is 3 to 10,000;

(Chemical formula 2)

$$R^3R^4{}_nSiX_{(3-n)} \quad (2)$$

wherein $R^3$ is selected from the group consisting of a $C_1$-$C_{20}$ monovalent hydrocarbon group, an amino group, an aminoethyl group, a mercapto group, an isocyanate and a phenyl group, $R^4$ is selected from the group consisting of a phenyl group, a hydrogen atom, and a $C_1$-$C_3$ monovalent lower alkyl group, X is a hydroxyl group or an alkoxy group, and n is 0 or 1;

(Chemical formula 3)

$$R^5{}_3SiO-(R^5{}_2SiO)_n-SiR^5{}_3 \quad (3)$$

wherein $R^5$ is a hydrolyzable group or a non-substituted or substituted $C_1$-$C_{20}$ monovalent hydrocarbon group, the hydrolyzable group is a hydroxyl group, an amino group, an acetoxy group, an alkoxyl group or a hydrogen atom, n is 3 to 1,000, and at least three hydrolyzable groups are provided in one molecule, a ratio between the diorganopolysiloxane with the reactive opposite ends and the crosslinking agent is in a compounding range of 100/0.1 to 100/35 wt %, and the silicone gel has a finely three-dimensional crosslinking structure of the diorganopolysiloxane, and when the silicone gel is obtained by effecting the method in the absence of the plate-like powder, the silicone gel has a complex modulus of 3,000 to 100,000 Pa and a loss coefficient tan δ of 1.0 to 2.5 in measurement of a dynamic viscoelasticity of a distortion factor of 17% at 25° C. and at a shear frequency of 4 Hz, and a measured value of the silicone gel measured by a measuring method with a durometer AO is 0.

2. The cosmetic plate-like powder surface-treated with the silicone gel set forth in claim 1, wherein the silicone gel is deposited and thermally fixed onto surfaces of particles of a plate-like powder as a starting material in an in-situ method in the presence of a plate-like powder by hydrolyzing/condensing at least a part of a mixture of (i) the diorganopolysiloxane with the reactive opposite ends of the formula (1) and (ii) the at least one crosslinking agent selected from the group consisting of (a) the silane coupling agent having the formula (2) and at least two hydrolyzable groups per one molecule and (b) the reactive organopolysiloxane of the formula (3).

3. The cosmetic plate-like powder surface-treated with the silicone gel set forth in claim 1, wherein the diorganopolysiloxane with the reactive opposite ends is used in the form of a water emulsion.

4. The cosmetic plate-like powder surface-treated with the silicone gel set forth in claim 1, wherein the cosmetic plate-like powder surface-treated with the silicone gel is obtained through hydrolyzing/condensing at least a part of (i) the diorganopolysiloxane having the opposite reactive ends of the formula (1) and (ii) the at least one crosslinking agent selected from the group consisting of (a) the silane coupling agent having the formula (2) and at least two hydrolyzable groups per one molecule and (b) the reactive organopolysiloxane of the formula (3) in a step:

(A) by mixing a water-soluble solvent and the cosmetic plate-like powder as the starting material, and separately or simultaneously adding (i) the diorganopolysiloxane with the reactive opposite ends expressed by the formula (1) and (ii) the at least on crosslinking agent selected from the group consisting of (a) the silane coupling agent having the formula (2) and at least two hydrolyzable groups per one molecule and (b) the reactive organopolysiloxane of the formula (3) in a state that the water-soluble solvent and the cosmetic plate-like powder are mixed and the mixed state of the water-soluble solvent and the cosmetic plate-like powder is either a capillary or slurry, or (B) by adding the crosslinking agent selected from the group consisting of (a) the silane coupling agent having the formula (2) an at least two hydrolyzable groups per one molecule and (b) the reactive organopolysiloxane of the formula (3) in the presence of the cosmetic plate-like powder as the starting material in the state that the water-soluble solvent, the cosmetic plate-like powder, and the diorganopolysiloxane of the formula (1) are mixed and the mixed state thereof is a capillary, followed by thermally fixing under heating at a temperature of 100 to 180° C. and pulverizing.

5. The cosmetic plate-like powder surface-treated with the silicone gel set forth in claim 1, wherein the cosmetic plate-like powder is an inorganic powder, an organic powder or a composite powder thereof, and wherein the diorganopolysiloxane of the formula (1) is dimethiconol.

6. The cosmetic plate-like powder set forth in claim 1, wherein the weight ratio between the silicone gel and the cosmetic plate-like powder is 100/0.1 to 100/25.0.

7. The cosmetic plate-like powder set forth in claim 1, wherein the plate-like powder is one or more kinds selected from talc, sericite, mica, kaolin and a plate-like glittering powder.

8. The cosmetic plate-like powder set forth in claim 7, wherein the plate-like glittering powder is one or more kinds selected from a lame of a resin laminated powder, a titanium oxide-coated glass powder and a titanium oxide-coated synthetic gold mica.

9. The cosmetic plate-like powder set forth in claim 5, wherein a water emulsion obtained by mechanically emulsifying the dimethiconol having a number L of dimethyl siloxane units of 3 to 1,000 in the formula (1) is used as a starting material for the surface treatment.

10. The cosmetic plate-like powder set forth in claim 5, wherein a water emulsion obtained by emulsion polymerizing the dimethiconol having a number L of dimethyl siloxane units of 3 to 1,000 in the formula (1) is used as a starting material for the surface treatment.

11. The cosmetic plate-like powder set forth in any of claim 5, wherein a water emulsion of the dimethiconol obtained by emulsion polymerizing octamethyl cyclotetrasiloxane as a starting material is used as a starting material for the surface treatment.

12. The cosmetic plate-like powder set forth in claim 5, wherein a surface active agent is contained in the water emulsion of the dimethiconol, and said surface active agent contains at least an acylated amino acid.

13. The cosmetic plate-like powder set forth in claim 12, wherein a mixing weight ratio (B)/(A)×100 between the weight (B) of the surface active agent and that (A) of the dimethiconol in the water emulsion of the dimethiconol is less than 6.0.

14. The cosmetic plate-like powder set forth in claim 1, wherein the organic group $R^3$ of the silane coupling agent of the formula (2) is either an amino group or a phenyl group; and/or wherein the weight ratio between the silicone gel and the plate-like powder to be surface-treated is 100/0.1 to 100/25.0.

15. A cosmetic composition containing at least 0.1 wt % of the cosmetic plate-like powder surface-treated with the silicone gel as set forth in claim 1.

16. A method for producing a cosmetic plate-like powder surface-treated with a silicone gel, said method comprising:
treating surfaces of particles of a plate-like powder having an average particle diameter in the range of from 0.01 to 700 μm as a starting material with the silicone gel by forming the silicone gel thereon in an in-situ method that comprises hydrolyzing and condensing an organopolysiloxane containing at least (i) a diorganopolysiloxane with reactive opposite ends expressed by the following formula (1) and (ii) at least one crosslinking agent selected from the group consisting of (a) a silane coupling agent having the following formula (2) and at least two hydrolyzable groups per one molecule and (b) a reactive organopolysiloxane of the following formula (3):

(Chemical formula 1)

$$R^1R^2{}_2SiO\text{—}(R^2{}_2SiO)_L\text{—}SiR^1R^2{}_2 \quad (1)$$

wherein $R^1$ is a hydrolyzable group selected from the group consisting of a hydroxyl group, an amino group, an acetoxy group, an alkoxy group or a hydrogen atom, $R^2$ is a non-substituted or substituted $C_1$-$C_{20}$ monovalent hydrocarbon group, and L is 3 to 10,000;

(Chemical formula 2)

$$R^3R^4{}_nSiX_{(3-n)} \quad (2)$$

wherein $R^3$ is selected from the group consisting of a $C_1$-$C_{20}$ monovalent hydrocarbon group, an amino group, an aminoethyl group, a mercapto group, an isocyanate and a phenyl group, $R^4$ is selected from the group consisting of a phenyl group, a hydrogen atom, and a $C_1$-$C_3$ monovalent lower alkyl group, X is a hydroxyl group or an alkoxy group, and n is 0 or 1;

(Chemical formula 3)

$$R^5{}_3SiO\text{—}(R^5{}_2SiO)_n\text{—}SiR^5{}_3 \quad (3)$$

wherein $R^5$ is a hydrolyzable group or a non-substituted or substituted $C_1$-$C_{20}$ monovalent hydrocarbon group, the hydrolyzable group is a hydroxyl group, an amino group, an acetoxy group, an alkoxyl group or a hydrogen atom, n is 3 to 1,000, and at least three hydrolyzable groups are provided in one molecule;
a ratio between the diorganopolysiloxane with the reactive opposite ends and the crosslinking agent is in a compounding range of 100/0.1 to 100/35 wt %; and
thermally fixing the surface-treated cosmetic plate-like powder and pulverizing a resultant, wherein the silicone gel formed on the surfaces of the particles of the plate-like powder has a finely three-dimensional crosslinking structure of the diorganopolysiloxane, and
when the silicone gel is obtained by effecting the method in the absence of the plate-like powder, a complex modulus of 3,000 to 100,000 Pa and a loss coefficient tan δ is 1.0 to 2.5 in measurement of a dynamic viscoelasticity under a distortion factor of 17% at 25° C. and a shear frequency of 4 Hz, and a measured value of the silicone gel measured by a measuring method with a durometer AO is 0.

17. The method for producing the cosmetic plate-like powder surface-treated with the silicone gel set forth in claim 16, wherein the diorganopolysiloxane with the reactive opposite ends is used in the form of a water emulsion.

18. The method for producing the cosmetic plate-like powder surface-treated with the silicone gel set forth in claim 16, wherein the cosmetic plate-like powder surface-treated with the silicone gel is obtained through hydrolyzing/condensing at least a part of (i) the diorganopolysiloxane having the opposite reactive ends of the formula (1) and (ii) the at least one crosslinking agent selected from the group consisting of (a) the silane coupling agent having the formula (2) and at least two hydrolyzable groups per one molecule and (b) the reactive organopolysiloxane of the formula (3) in a step:

(A) by mixing a water-soluble solvent and the cosmetic plate-like powder as the starting material, and separately or simultaneously adding (i) the diorganopolysiloxane with the reactive opposite ends expressed by the formula (1) and (ii) the at least one crosslinking agent selected from the group consisting of (a) the silane coupling agent having the formula (2) and at least two hydrolyzable groups per one molecule and (b) the reactive organopolysiloxane of the formula (3) in a state that the water-soluble solvent and the cosmetic plate-like powder are mixed and the mixed state of the water-soluble solvent and the cosmetic plate-like powder is either a capillary or slurry, or (B) by adding the crosslinking agent selected from the group consisting of (a) the silane coupling agent having the formula (2) and at least two hydrolyzable groups per one molecule and (b) the reactive organopolysiloxane of the formula (3) under the presence of the cosmetic plate-like powder as the starting material in the state that the water-soluble solvent, the cosmetic plate-powder, and the diorganopolysiloxane of the formula (1) are mixed and the mixed state thereof is a capillary, followed by thermally fixing and pulverizing.

19. The method for producing the cosmetic plate-like powder surface-treated with the silicone gel set forth in claim 16, wherein the cosmetic plate-like powder is an inorganic powder, an organic powder or a composite powder thereof.

20. The method for producing the cosmetic plate-like powder set forth in claim 16, wherein the diorganopolysiloxane of the formula (1) is dimethiconol.

21. The method for producing the cosmetic plate-like powder set forth in claim 16, wherein the weight ratio between the silicone gel and the cosmetic plate-like powder is 100/0.1 to 100/25.0 in weight ratio.

22. The method for producing the cosmetic plate-like powder set forth in claim 16, wherein the silicone gel is obtained by hydrolyzing/condensing the diorganopolysiloxane having the opposite reactive ends of the formula (1) and the silane coupling agent of the formula (2) having at least two hydrolysable groups per one molecule.

23. The method for producing the cosmetic plate-like powder set forth in claim 20, wherein a water emulsion obtained by mechanically emulsifying the dimethiconol having a number L of dimethyl siloxane units of 3 to 1,000 in the formula (1) is used as a starting material for the surface treatment.

24. The method for producing the cosmetic plate-like powder set forth in claim 20, wherein a water emulsion obtained by emulsion polymerizing the dimethiconol having a number L of dimethyl siloxane units of 3 to 1,000 in the formula (1) is used as a starting material for the surface treatment.

25. The method for producing the cosmetic plate-like powder set forth in claim 20, wherein a water emulsion of the dimethiconol obtained by emulsion polymerizing octamethyl cyclotetrasiloxane as a starting material is used as a starting material for the surface treatment.

26. The method for producing the cosmetic plate-like powder set forth in claim 20, wherein a surface active agent is contained in the water emulsion of the dimethiconol, and the surface active agent contains at least an acylated amino acid.

27. The method for producing the cosmetic plate-like powder set forth in claim 26, wherein a mixing weight ratio (B)/(A)×100 between the weight of the dimethiconol (A) and the weight of a surface-active agent (B) in the water emulsion of the dimethiconol is less than 6.0.

28. The method for producing the cosmetic plate-like powder set forth in claim 16, wherein the organic group $R^3$ of the silane coupling agent of the formula (2) is either an amino group or a phenyl group.

29. A cosmetic composition containing at least 0.1 wt % of the cosmetic plate-like powder surface-treated with a silicone gel produced by the method as set forth in claim 16.

* * * * *